(12) United States Patent
Wiesendanger

(10) Patent No.: US 8,408,062 B2
(45) Date of Patent: Apr. 2, 2013

(54) STUD SCANNER

(75) Inventor: Markus Wiesendanger, Zürich (CH)

(73) Assignee: ALSTOM Technology Ltd., Baden (CH)

( * ) Notice: Subject to any disclaimer, the term of this patent is extended or adjusted under 35 U.S.C. 154(b) by 343 days.

(21) Appl. No.: 12/879,086

(22) Filed: Sep. 10, 2010

(65) Prior Publication Data

US 2011/0093988 A1 Apr. 21, 2011

(30) Foreign Application Priority Data

Sep. 15, 2009 (CH) ...................................... 1423/09

(51) Int. Cl.
*G01N 29/04* (2006.01)
(52) U.S. Cl. ............................................ 73/618; 73/623
(58) Field of Classification Search .................... 73/618, 73/623
See application file for complete search history.

(56) References Cited

U.S. PATENT DOCUMENTS

| 4,481,814 A | 11/1984 | Wentzell |
| 7,531,770 B2 | 5/2009 | Tanaka et al. |
| 2007/0146463 A1 * | 6/2007 | Sasa .............................. 347/104 |

FOREIGN PATENT DOCUMENTS

| EP | 0242947 | 10/1987 |
| EP | 0331944 | 9/1989 |
| JP | 2002031624 | 1/2002 |

OTHER PUBLICATIONS

Search Report for Swiss Patent App. No. 01423/09 (Jan. 11, 2010).

* cited by examiner

*Primary Examiner* — Hezron E Williams
*Assistant Examiner* — Paul West
(74) *Attorney, Agent, or Firm* — Cermak Nakajima LLP; Adam J. Cermak

(57) ABSTRACT

A scanning device (36) is useful for scanning a body, especially a stud (10), from a bore (13) which extends through the body or stud (10) and is accessible from the outside. The scanning device (36) includes a probe (15) which is fastened on a cylindrical rod (14) and can be inserted into the bore (13) for scanning the body or stud (10), which probe, by displacing the rod (14) in its longitudinal direction is longitudinally displaceable in the bore (13), and by rotating the rod (14) around its cylinder axis (34) is rotatable around the bore axis. A compact and light construction, and flexible applicability, are achieved by a compact, controllable drive unit (20), through which the rod (14) extends and which longitudinally displaces and/or rotates the rod (14) depending upon selection, for displacing and rotating the rod (14).

12 Claims, 3 Drawing Sheets

STUD SCANNER

This application claims priority under 35 U.S.C. §119 to Swiss application number 01423/09, filed 15 Sep. 2009, the entirety of which is incorporated by reference herein.

BACKGROUND

1. Field of Endeavor

The present invention relates to the field of non-destructive workpiece testing, and more particularly to a scanning device.

2. Brief Description of the Related Art

In the technology of thermal machines, especially steam or gas turbines, studs are frequently used for screwing together turbine casings which have a bore extending in the longitudinal direction in order to be able to heat up the stud separately, for example. Cracks can extend from this bore, which impair the mechanical strength of the stud which is under severe stress and can lead to serious consequences.

It has therefore already been proposed in the past to visually inspect such studs by an optical probe being inserted into the bore after preparatory cleaning of the bore and preparation of the inside surface (U.S. Pat. No. 7,531,770). A visual inspection of this type, however, is associated with considerable expenditure of time during preparation and execution, cannot be easily automated, and is comparatively unreliable because only the surface can be inspected.

There are additional devices known on the market for the inspection of such bores by ultrasound, which are referred to as "Stud Inspection Manipulators" (SIM) (Phoenix Inspection Systems Ltd., Warrington, UK). In the case of these known devices, the sensor head of the ultrasound device is fastened on one end of a rod which by the other end is connected to a first drive unit by which the rod can be rotated in a controlled manner around the longitudinal axis. The first drive unit in turn is mounted on a slide which by a controllable, second drive unit can be moved linearly on a rail in the longitudinal direction of the rod. This device allows a detailed, automated and reliable inspection of the body, but has the disadvantage that, owing to the comparatively large external dimensions, it is unmanageable during transportation and requires a lot of space on the inlet side of the bore and also is limited with regard to the axial scanning range because of the length of the rail.

SUMMARY

One of numerous aspects of the present invention includes a scanning device of the aforementioned type, which can overcome the described disadvantages of known devices and is compact, operation which can be automated, and is highly flexible when used.

Another aspect of the present invention includes, for displacing and rotating the rod, a compact, controllable drive unit through which the rod extends and which longitudinally displaces and/or rotates the rod depending upon selection. The (combined) drive unit which is responsible for the two types of movement (rotation and linear displacement) of the rod enables the dispensing of heavy and bulky slides and linear guides. Since the rod extends through the drive unit, the scanning range can be flexibly designed without special measures.

Another aspect of the invention includes that the drive unit includes a first screw drive which, during a rotation around the cylinder axis of the rod in a first rotational direction, longitudinally displaces the rod in a first direction, and during a rotation around the cylinder axis of the rod in an opposite, second rotational direction, longitudinally displaces the rod in an opposite, second rotational direction, the drive unit includes a second screw drive which, during a rotation around the cylinder axis of the rod in the first rotational direction, longitudinally displaces the rod in the second direction, and during a rotation around the cylinder axis of the rod in the second rotational direction, longitudinally displaces the rod in the first direction, and the two screw drives are connected to a common control unit.

Another aspect includes that the screw drives each have a bearing ring which concentrically encompasses the rod and is rotatably mounted around the cylinder axis in a common housing, and in each of the bearing rings a multiplicity of friction rollers are rotatably mounted around the rod in a uniformly distributed manner in the style of planetary gearwheels, in such a way that they roll on the external surface of the rod with frictional engagement, the rotational axes of the friction rollers of a bearing ring are tilted in each case by the same angle in relation to the cylinder axis, and the rotational axes of the friction rollers of the two bearing rings are tilted either in the same direction or in the opposite direction.

The rod is preferably guided in the housing in the axial direction, for example by plain bearings.

Another aspect includes that means are provided on the housing for fastening the scanning device on the body or stud.

The fastening means preferably includes a flange which is adapted to the body or stud.

According to a further aspect, each of the screw drives has a separate, controllable drive.

Another aspect includes that the probe is designed for non-destructive testing of the body or stud by ultrasound and is connected to a corresponding measuring unit. Other inspection methods, such as eddy current measurement, are also conceivable.

Scanning devices embodying principles of the present invention are especially simple and stable in construction if, according to another development, the probe is fastened directly on one end of the rod.

In order to be able to detect and take into consideration slip which occurs in a frictional engagement between screw drives and rod, it is advantageous if, according a further aspect, means are provided for determining the position of the rod relative to the drive unit. In this case, the rotational and linear movements of the rod can be received and evaluated, for example in the manner of an optical mouse.

BRIEF DESCRIPTION OF THE DRAWINGS

The invention shall be explained in more detail in the following text based on exemplary embodiments in conjunction with the drawing. In the drawing

DETAILED DESCRIPTION OF EXEMPLARY EMBODIMENTS

Figure 1:
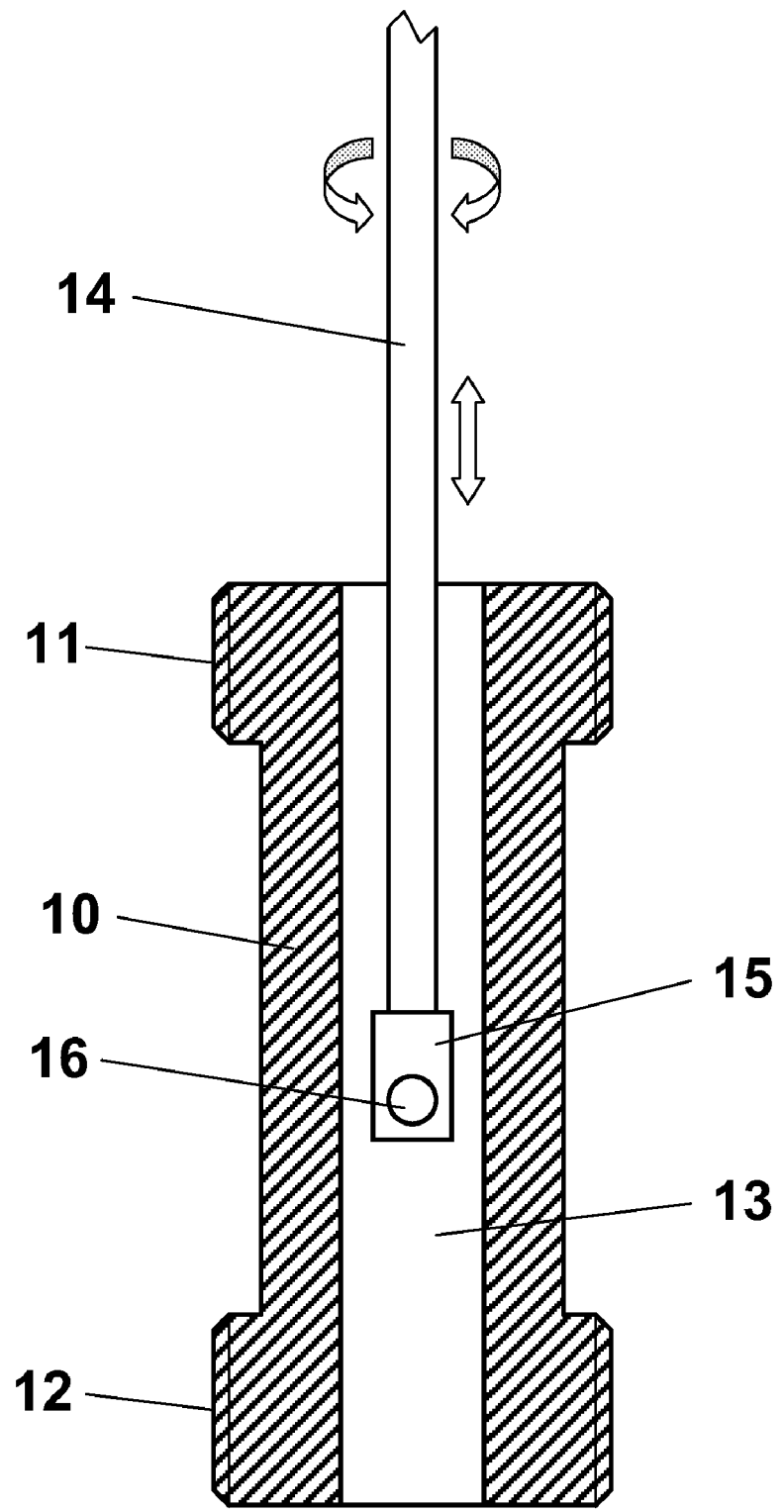
FIG. 1 shows an example of a scanning situation, for which the scanning device according to the invention can be used.

FIG. 1 shows an example of a scanning situation for which the scanning device according to principles of the present invention can be used. A stud 10, which serves for the screwed fastening of a turbine casing and is provided with two male threads 11 and 12 at the ends, is to be inspected in this case. A bore 13 extends through the stud and can be used for example for heating up the stud 10 from the inside for thermal adaptation to the turbine. It is self-evident that other scanning situations are also conceivable, in which from a bore or a passage in a body the body is inspected for damage.

For inspecting the stud 10, a probe 15, which is fastened on a rod 14, is inserted into the bore 13 of the stud 10, which probe is formed for example as an ultrasound probe, and through an opening 16 transmits and receives ultrasound signals in a specific direction perpendicularly to the rod axis. Other types of non-destructive testing are also conceivable, however.

The entire inner side of the bore 13 can be scanned by the probe 15 being displaced on the rod 14 in the longitudinal direction of the rod and/or by the probe being rotated around the rod axis in an angular range of at least 360° (see arrows in FIG. 1). For this combined linear and rotational movement, devices and processes embodying principles the present invention now provide a drive solution which is compact and flexible in application, which enables the scanning device to be easily transported to a place of use which is limited by space and to be used there in the widest variety of configurations without great effort.

Figure 2:
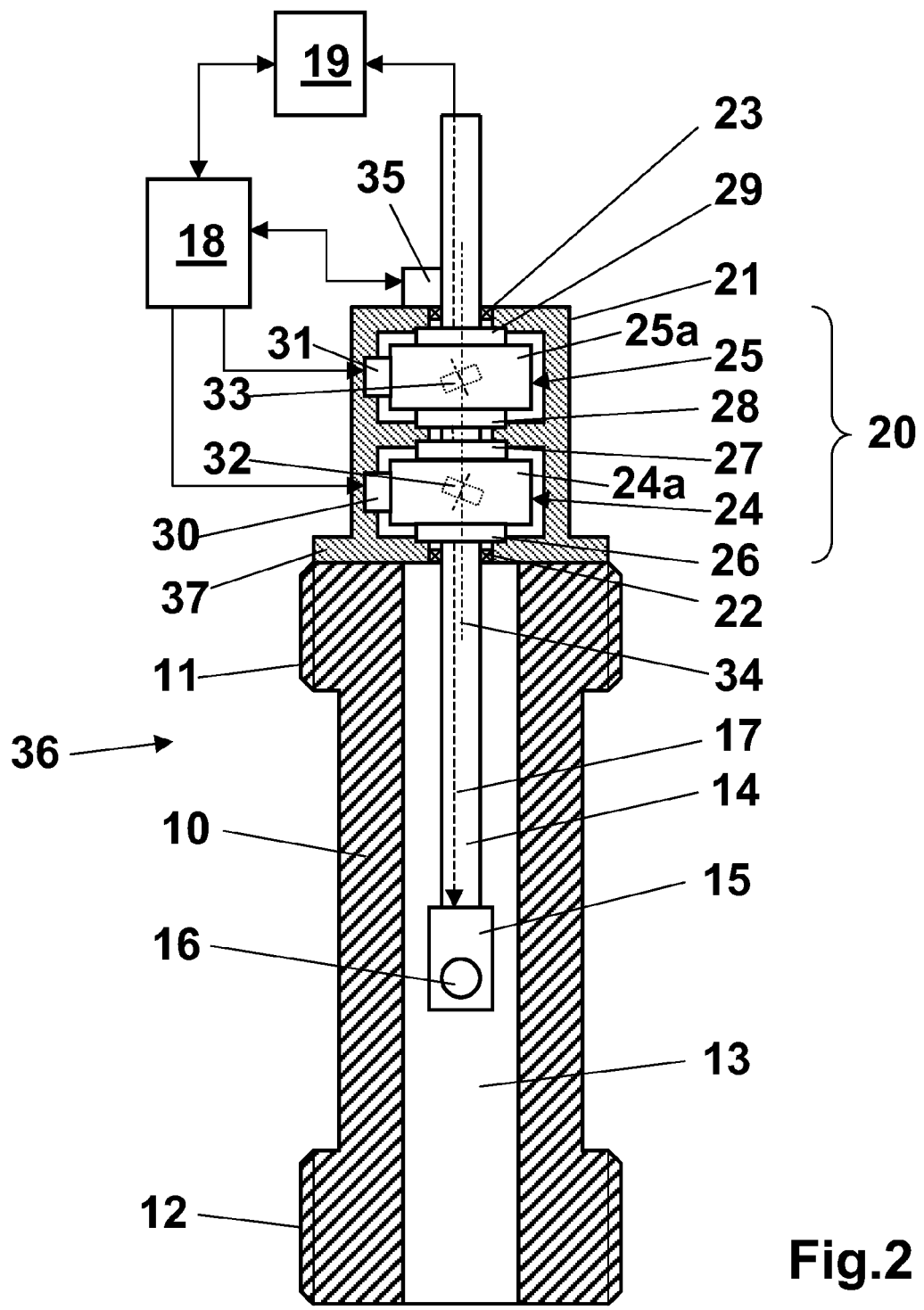
FIG. 2 shows an exemplary embodiment of a scanning device according to the invention in use in the scanning situation according to FIG. 1.

FIG. 2 shows (in partial longitudinal section) an exemplary embodiment of the scanning device according to principles of the invention, in use on a stud, as has already been shown in FIG. 1. The scanning device 36 of FIG. 2 includes the probe 15, which is fastened on the front end of the cylindrical rod 14, and also a compact drive unit 20 which, by a flange 37 (for example with a cap nut which is not shown in FIG. 2) which is provided for it, can be detachably fastened on the stud 10 which is to be inspected.

The drive unit 20, through which the rod 14 extends in the middle, is accommodated in a housing 21. The penetrating rod 14 is rotatably and linearly displaceably mounted in an upper and a lower opening in the housing 21 by corresponding plain bearings 22 and 23. Two screw drives 24 and 25, which on account of their design convert a rotational movement around the axis 34 into a linear movement of the rod 14 in the direction of the axis 34, are accommodated in the housing 21 one behind the other in the axial direction (axis 34), wherein a reversal of the rotational movement also results in a reversal of the linear movement.

The two screw drives 24 and 25 operate contrarotationally, i.e., with the same rotational direction they move the rod 14 in the same way but in opposite axial directions, whereas with opposite rotational directions they displace the rod 14 in the same axial direction. In this case, different situations are distinguishable (if for the sake of simplicity the same pitch is assumed in the two screw drives):

If the rotational direction and the rotational speed of the two screw drives 24, 25 are the same, the axial linear movements of the rod 14 are cancelled out and the rod 14 rotates at the same rotational speed around its axis.

If the rotational direction of the two screw drives 24, 25 is the same, but the rotational speeds differ, an axial linear movement, the direction of which is determined by the screw drive with the higher rotational speed, is superimposed upon the rotational movement in the rod 14.

If the rotational direction of the two screw drives 24, 25 is opposite and the rotational speed is the same, the rod 14 moves at maximum speed exclusively in the axial direction without executing a rotational movement.

If the rotational direction of the two screw drives 24, 25 is opposite and the rotational speed is different, the rod 14 moves in the axial direction and executes a rotational movement, the direction and speed of which depends upon which of the two screw drives 24, 25 has the higher rotational speed.

By individual controlling of the two screw drives 24, 25, any combination of linear and rotational movement of the rod 14 can thus be created, with which any point on the inner side of the bore 13 can be approached with the probe 15.

Figure 3:
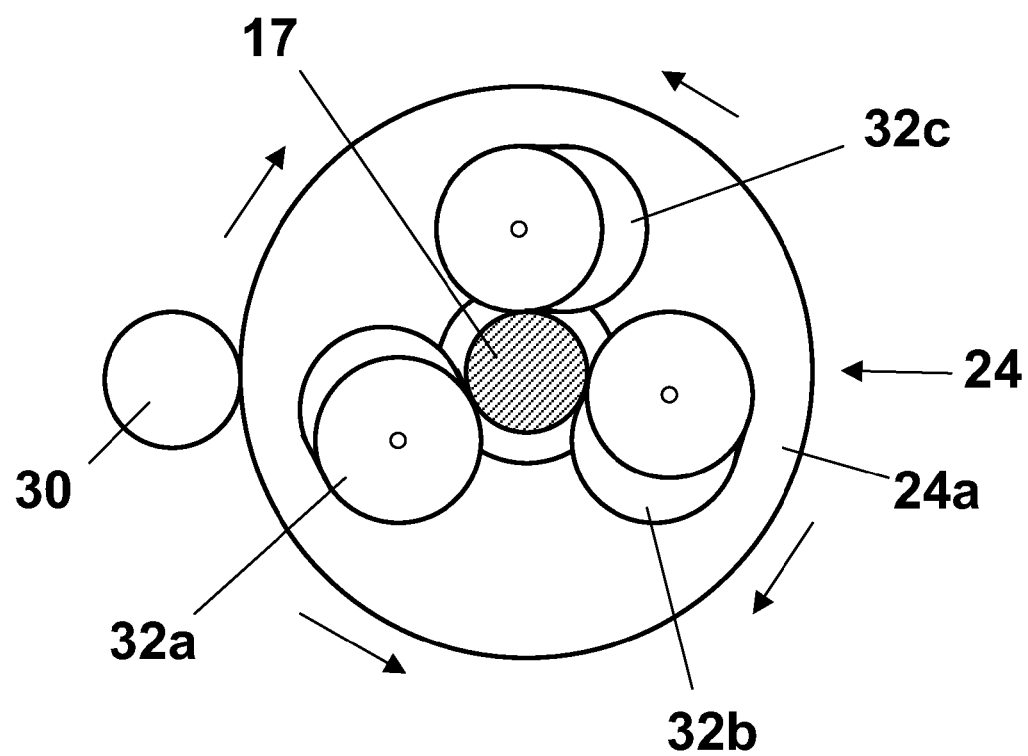
FIG. 3 shows the plan view in the axial direction of an exemplary arrangement of the friction rollers in one of the screw drives from FIG. 2.

A simple type of screw drive can be realized by a motor-powered bearing ring 24a or 25a which is rotatably mounted in the housing 21 by ball bearings 26, 27 and 28, 29, which bearing ring encompasses the rod 14 concentrically and with clearance, and in which, with tilted axis, friction rollers 32, 33 (in FIG. 2) or 32a-c (in FIG. 3), which are distributed over the circumference, are rotatably mounted and roll on the external surface of the rod 14 by frictional engagement if the associated bearing ring is rotated. According to FIG. 3, three friction rollers 32a-c per screw drive 24, 25, offset in each case by 120°, are arranged in the bearing ring. For the rotational drive of the bearing ring, provision can be made for example for a drive motor 30 or 31 which (for example as a servo motor) is controlled by a control unit 18. The contrarotatability of the screw drives 24, 25 is achieved by the axes of the friction rollers 32, 33 (as indicated in FIG. 2 with dotted lines) being tilted from the axis 34 in opposite directions. The accuracy of positioning of the probe 15 in this case increases as the tilt angle of the axes decreases.

The probe 15 is connected via a measuring lead 17 to a measuring unit 19. The measuring lead 17 in this case is expediently guided through the inside of the rod 14 to the probe 15. Measuring unit 19 and control unit 18 may be interconnected in order to be able to associate coordinates with the measuring points. Since on account of the friction rollers a slip may occur between screw drive and rod, it is advantageous to arrange a displacement transducer 35 on the rod 14, which, for example in the style of an optical mouse, senses the linear and rotational movement of the rod 14 and directs it to the control unit 18.

The probe 15 can be detachably fastened on the end of the rod in order to be able to use other probe sizes in the case of varying bore diameters. Likewise, the rod 14 can be altered in length in order to be able to scan bores with greater axial length. The drive unit 20 in this case, on account of its construction and its principle of operation, does not need to be modified. Instead of a rigid rod, it is also conceivable to use a flexible rod, which is bendable to a lesser or greater degree, in order to be able to scan bodies with curved passages.

Overall, scanning devices embodying principles of the present invention can be characterized by the following characteristics and advantages: light and compact type of construction; no moving drive motors; long rod lengths possible without modification of the drive unit; and use of flexible rods are possible.

LIST OF DESIGNATIONS

10 Stud
11, 12 Male thread
13 Bore
14 Rod
15 Probe (for example ultrasound)
16 Opening
17 Measuring lead
18 Control unit
19 Measuring unit
20 Drive unit
21 Housing
22, 23 Plain bearing 24, 25 Screw drive
24a, 25a Bearing ring
26, . . . , 29 Ball bearing
30, 31 Drive motor
32, 33 Friction roller
32a-c Friction roller
34 Axis (cylinder axis)
35 Displacement transducer
36 Scanning device
37 Flange While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

I claim:

1. A scanning device useful for scanning a body having a bore which extends through the body and is accessible from outside the body, the scanning device comprising:
    a cylindrical rod having a longitudinal cylinder axis;
    a probe fastened on the rod and configured and arranged to be inserted into the bore for scanning the body, which probe, by displacing the rod in its longitudinal direction, is axially displaceable in the bore, and by rotating the rod around its cylinder axis, is rotatable around the bore axis;
    a controllable drive unit configured and arranged to longitudinally displace and rotate the rod, the rod extending through the drive unit;
    a control unit;
    wherein the drive unit comprises a first screw drive which, during rotation around the rod cylinder axis in a first rotational direction, longitudinally displaces the rod in a first direction, and during rotation around the rod cylinder axis in an opposite, second rotational direction, longitudinally displaces the rod in an opposite, second direction;
    wherein the drive unit comprises a second screw drive which, during rotation around the rod cylinder axis in the first rotational direction, longitudinally displaces the rod in the second direction, and during rotation around the rod cylinder axis in the second rotational direction, longitudinally displaces the rod in the first direction; and
    wherein the two screw drives are connected to the control unit.

2. The scanning device as claimed in claim 1, further comprising:
    a common housing; and
    wherein the screw drives each comprise a bearing ring which concentrically encompasses the rod and is rotatably mounted around the rod cylinder axis in the common housing;
    wherein each of the bearing rings comprises a multiplicity of friction rollers rotatably mounted around the rod in a uniformly distributed manner as planetary gearwheels so that said rollers roll on the external surface of the rod with frictional engagement, each friction roller having a rotational axis;
    wherein the rotational axes of the friction rollers of each bearing ring are tilted by the same angle relative to the cylinder axis; and
    wherein the rotational axes of the friction rollers of the two bearing rings are tilted either in the same direction or in the opposite direction.

3. The scanning device as claimed in claim 2, further comprising axial guides which guide the rod in the housing in the axial direction.

4. The scanning device as claimed in claim 3, further comprising:
    means on the housing for fastening the scanning device on the body to be inspected.

5. The scanning device as claimed in claim 4, wherein the fastening means comprises a flange adapted to the body.

6. The scanning device as claimed in claim 1, further comprising:
    a separate, controllable drive for each of the screw drives.

7. The scanning device as claimed in claim 1, further comprising:
    a measuring unit; and
    wherein the probe comprises a non-destructive ultrasonic testing probe and is connected to the measuring unit.

8. The scanning device as claimed in claim 1, wherein the probe is fastened directly on one end of the rod.

9. The scanning device as claimed in claim 1, further comprising:
    means for determining the position of the rod relative to the drive unit.

10. The scanning device as claimed in claim 9, wherein the means for determining the position of the rod comprises an optical transducer.

11. The scanning device as claimed in claim 9, further comprising:
    a control unit in control communication with the controllable drive unit; and
    wherein the means for determining the position of the rod is in communication with the control unit.

12. A method of inspecting a stud, the stud including a cylindrical body with two opposite ends, external threads on both of said ends, and a bore extending entirely through the body between the ends, the method comprising:
    providing a scanning device according to claim 1;
    positioning said probe in said bore; and
    scanning at least a portion of said stud with said probe from within said bore.

* * * * *